United States Patent [19]

Hayes et al.

[11] Patent Number: 5,695,807
[45] Date of Patent: Dec. 9, 1997

[54] 4-ALLYLANISOLE ANALOG SCOLYTID REPELLENTS

[75] Inventors: Jane L. Hayes; Brian L. Strom, both of Pineville; Lawrence Roton, Pollock, all of La.; Leonard L. Ingram, Starkville, Miss.

[73] Assignees: The United States of America as represented by the Secretary of Agriculture, Washington, D.C.; Mississippi State University, Mississippi State, Miss.

[21] Appl. No.: 625,978

[22] Filed: Apr. 1, 1996

Related U.S. Application Data

[63] Continuation-in-part of Ser. No. 358,707, Dec. 19, 1994, Pat. No. 5,518,757, which is a continuation-in-part of Ser. No. 113,709, Aug. 31, 1993, Pat. No. 5,403,863.

[51] Int. Cl.$^6$ ............ A01N 25/00; A01N 25/08; A01N 25/18; A01N 31/14
[52] U.S. Cl. ............ 427/4; 424/405; 424/409; 514/919

[58] Field of Search ............ 427/4; 424/84, 424/405, 409; 514/919, 717

[56] References Cited

U.S. PATENT DOCUMENTS

| | | | |
|---|---|---|---|
| 3,876,762 | 4/1975 | Rabussier et al. | 424/78 |
| 4,219,570 | 8/1980 | Inazuka et al. | 424/343 |
| 4,782,094 | 11/1988 | Numata et al. | 514/721 |
| 4,855,127 | 8/1989 | Abrutyn et al. | 424/411 |
| 5,250,574 | 10/1993 | Sakamoto et al. | 514/721 |

*Primary Examiner*—Diana Dudash
*Attorney, Agent, or Firm*—Oblon, Spivak, McClelland, Maier & Neustadt, P.C.

[57] ABSTRACT

4-allylanisole, and seven analogs, anisole, allylbenzene, 4-isopropylanisole, p-anisaldehyde, ethylbenzene, cumene and 4-methoxyacetophenone are demonstrated to be effective repellents for scolytid infestation. Conifers, a particular target for the scolytids, are protected by application of the compounds, either directly or suspended in a carrier.

3 Claims, No Drawings

4-ALLYLANISOLE ANALOG SCOLYTID REPELLENTS

RELATED PATENT APPLICATIONS

This application is a continuation-in-part of U.S. patent application Ser. No. 08/358,707 filed Dec. 19, 1994, now U.S. Pat. No. 5,518,757, which is in turn a continuation-in-part application of U.S. patent application Ser. No. 08/113,709 filed Aug. 31, 1993, now U.S. Pat. No. 5,403,863. The entire disclosure of that application and that patent is incorporated herein, by reference.

BACKGROUND OF THE INVENTION

In applicants' pending application U.S. Ser. No. 08/358,707 filed Dec. 19, 1994, the effectiveness of 4-allylanisole, anisole, allylbenzene and 4-isopropylanisole as a repellent for Scolytidae in general is examined at length. Insect attack on healthy, damaged or weakened host trees, such as loblolly pines and other host trees (including eastern and western white pines, all yellow pines (eastern and western species) Norway spruce, Larch, eastern red cedar, eastern Hemlock, Fraser fir, Douglas fir, and other fir trees, and thus generally conifers) continues to be a significant commercial and ecological problem. Although certain insecticides have been established for limited protection of trees, the use of non-natural chemical insecticides itself has serious impacts on the environment, and ought to be avoided, where possible. In particular, the use of a limited number of chemicals increases the risk of development of resistance in the pest population, alters the ecosystem by reducing species diversity, modifying the food chain and altering patterns of energy flow and nutrient cycling, and may adversely affect natural enemies of these beetles, (the southern pine beetle, and conifer-feeding members of the beetle family, Scolytidae in general). Coupled with the ecological dangers of using an insecticide is the fact that the high cost of labor and the high cost of the chemical products, along with the need to spray all surfaces for effective control will generally restrict the use of topically applied chemicals.

Thus, applicants' identification in the parent application of 4-allylanisole and selected analogous repellents to scolytids, 4-allylanisole being a naturally produced component of the resin exuded by the potential host tree, provides an alternate method of protecting these hosts, which does not require spraying of all potential surfaces. In particular, application of the product as a concentrated liquid, carried on elution devices or applied directly to a portion of the tree, as a vapor or as a powder, may be used with good effectiveness.

The prior art in this field has, as a result of the desirability of selecting naturally-produced products, focused on semiochemicals, both insect and host produced. Specifically, of all the references discussed in the parent and grand-parent application which discussed host-produced compounds, Werner, *Journal of Insect Physiology*, 18:423–438, 1972 is perhaps the most complete. This reference identifies 4-allylanisole as an attractant for *Ips grandicollis* in purified form at 1% concentration. The article teaches one of skill in the art that an effective repellent for Scolytidae employing 4-allylanisole cannot be prepared. However additional research by the author of the reference, Werner, *Environmental Entomology*, 24:372–379, 1995 has in fact documented the discovery disclosed in the pending parent application, that 4-allylanisole is a repellent for scolytids.

In general, to be an effective Scolytid repellent, the compound in question must significantly reduce the number of beetles attracted to a host tree. Host trees are not killed by individual beetles, rather through the process of mass attack by a large number of beetles. Thus, only those compounds that repel in excess of 50% of the subject insects to which it is exposed in a given trial were considered effective.

Accordingly, it remains an object of those of skill in the art to develop alternatives to conventional insecticides, employing compounds selected from, or similar to, those naturally produced by the targeted host, as effective insect repellents.

SUMMARY OF THE INVENTION

Applicants' invention resides in the discovery that an expanded family of compounds including 4-allylanisole are effective in repelling southern pine beetles as well as related conifer-feeding scolytids. Specifically, in addition to those compounds discussed in parent application 08/358,707 (anisole, allylbenzene, 4-allylanisole and 4-isopropylanisole), p-anisaldehyde, ethylbenzene, cumene and 4-methoxyacetophenone repel in excess of 50% of the southern pine beetles exposed to the same, in laboratory tests established as having a high correspondence with field trials. Surprisingly, other closely related analogs showed little or no repellency when tested under identical conditions. The chemical compounds named above can be prepared in the form of an insect repellent for the protection of conifers subject to scolytid attack. Methods of controlling scolytid attack using these effective compounds, which are either naturally produced or closely correlated to naturally produced compounds, include applying the compound to the surface of the tree or other host as either a liquid, or powder or other particulate form, alone or in an environmentally compatible carrier, or applying solid supports, such as cloth wicks from which the repellent chemical is eluted, or dispersed as vapor, in areas proximate or adjacent to the surface from which the scolytids are to be repelled. Vulnerable trees, bearing wounds, such as those produced by lightning strikes and woodpecker activity, can be protected by application to the exposed area. Similarly, at-risk single trees, and stands of tress can be protected by the effective use of these environmentally-neutral compounds.

DETAILED DESCRIPTION OF THE INVENTION

To test the effectiveness of insect repellents, a laboratory assay was employed, which assay has been demonstrated to be highly correlated with field trials Hayes et al., *J. Chem. Ecol.* 20(7):1595–1615, 1994, Hayes & Strom, *J. Economic Entomology* 87(6) 1586–1594, 1994, and Werner, *Env. Ent.* 24:372–379, 1995. Specifically, a circle (17 cm in diameter by 5 mm wide) of the potential repellent was painted with a camel-hair brush on a 28×21.5 cm piece of uncoated cardboard. After 3 minutes, beetles (2–5 individuals) were released in the center of the treated circle. Testing was conducted at room temperature (22°–25°) with light supplied from an adjoining room. To prevent overwhelming photopositive responses, an object was used to cast a shadow over the test circle. Beetles were briefly refrigerated prior to testing to reduce their tendency to fly. Responses (up to 30 second exposure) were recorded as not-repelled or repelled: not-repelled beetles walked through the circle or proceeded across the circle within 30 seconds of exposure; repelled beetles stopped abruptly, raised antennae (some "reared up" on hind legs), stood motionless and/or moved away from the circle (some moved abruptly in the opposite direction).

The results of these trials were combined far presentation in Table 1. In all trials, only apparently healthy beetles were used. Each analog was tested as described above. No less than 25 insects were used in each analog trial, totalling over 300 insects.

As is clearly shown in Table 1, well over 50% of scolytid were effectively repelled by the compounds of the invention. As shown in the parent and grand-parent applications, these repellents are at least as effective as commercially and experimentally available compounds, repelling scolytids in percentages at least as great as those repelled by the experimentally available anti-aggregant, verbenone. In point of fact, against the southern pine beetle (SPB), verbenone was remarkably ineffective, repelling less than 15% of the beetles in a laboratory setting, while 4-allylanisole, anisole, allylbenzene, 4-isopropylanisole and 4-methoxyacetophenone gave an approximate 90% or better repellency value and p-anisaldehyde, ethylbenzene and cumene gave high repellency values. Each of these compounds elicited an obvious and dramatic repelled behavior from those beetles responding.

The result of testing is set forth in Table 1 ("Results of Analog Testing"). Surprisingly, eight of the compounds performed as well or better than the repellency standard in repelling over 50% of the insects. Anisole, allylbenzene, 4-isopropylanisole, 4-allylanisole and 4-methoxyacetophenone proved remarkably effective as repellents for the southern pine beetle. P-Anisaldehyde, ethylbenzene and cumene were also effective. Equally surprising, fourteen other closely related structural analogs were demonstrated to be ineffective in repelling the scolytids. An effort was made to screen analogous chemical compounds that in previous studies by those skill in the art, showed biological activities (either attractant or repellent) for arthropods in other systems, such as corn rootworm. The essential characteristic of the chemical structure of a scolytid repellent is not apparent from these tests alone. Thus, it is not apparent nor obvious from chemical structure which analogs will exhibit repellency.

The laboratory studies conducted have been well documented as effective predictors of field performance (Hayes et al., Hayes and Strom, supra). These studies include protection of at risk pine trees with the inventive repellents such as lightning-struck pine trees or pine tress with cavities due to red-cockaded woodpecker activity. No protected trees were successfully attacked by any scolytid. Additionally, 90% protection of threatened pines at the urban/forest interface was achieved. This, as well as the results of independent investigators, Werner, *Env. Ent.* 24:372-379, 1995, have led those in the field to conclude that the laboratory assay described above is recognized as a valid determinant of a species response.

Of further importance is the fact the repellents of this invention, 4-allylanisole and the effective analogs, do not repel, and apparently do not affect, a predator of scolytids, the clerid beetle *Thanasimus dubius*. Thus, the repellents of the claimed invention, either chemicals naturally produced by target conifer hosts, or chemical analogs thereof, are environmentally sound and they are at least as effective as the predominant experimental compound available, insect-produced anti-aggregant verbenone. This information demonstrates that the claimed compounds provide a compelling alternative to insecticides because they do not disturb naturally-occurring predators. Thus, these compounds are superior biologically-efficient conifer-protectants.

The repellent can be prepared either as a neat preparation, or powder, or admixed with an environmentally compatible carrier, or as solid wick or polymer mass impregnated with the repellent compound which is released therefrom. Application of sprays and prepared suspensions to trees may additionally be effective. A minimum effective concentration of the compound may be 0.01 percent, but greater concentrations, on up to 100 percent can be employed.

The compounds are typically used in the lowest possible concentration while at the same time achieving effective repellency. In some situations, however, higher concentrations may be necessary or desirable. Factors to be considered include repellency rate, method of treatment, local weather conditions, stage and size of infestation and other factors known to those of skill in the art.

Mixtures of the compounds of the invention may also be used. If mixtures are used, those of skill in the art will adjust the mixture to reflect the desired repellency rate, product cost, treatment method, scolytid and conifer species targeted for treatment, and other factors known to those of skill in the art.

This invention has been disclosed and described above with reference to both specific examples and generic concept. Alternatives will occur to those with skill in the art, particularly with respect to concentration, environmentally compatible carrier and method of administration, without departing from the scope of the invention, save as limited by the claims set forth below.

TABLE 1

RESULTS OF ANALOG TESTING

| Repellent Compound | % of Scolytids Repelled |
| --- | --- |
| 1. 4-Allylanisole | 100 |
| 2. Anisole | >80 |
| 3. Allylbenzene | >90 |
| 4. 4-Isopropylanisole | >90 |
| 5. P-Anisaldehyde | 65 |
| 6. Ethylbenzene | 72 |
| 7. Cumene | 55 |
| 8. 4-Methoxyacetophenone | 96 |
| 9. Trans-Anethole | <20 |
| 10. 4-Methoxycinnamonitrile | <20 |
| 11. 4-Methoxyphenylacetonitrile | <30 |
| 12. Eugenol | <40 |
| 13. 2-Methylanisole | 35 |
| 14. 4-Methylanisole | 45 |
| 15. Butylbenzene | 39 |
| 16. Propylbenzene | 17 |
| 17. 2-Methoxbenzyl alcohol | 0 |
| 18. 3-Methoxbenzyl alcohol | 0 |
| 19. 4-Methoxbenzyl alcohol | 0 |
| 20. 2-Methoxyacetophenone | 8 |
| 21. 3-Methoxyacetophenone | 8 |
| 22. 4-Vinylanisole | 24 |

What is claimed is:

1. A method of repelling conifer-feeding beetles of the family Scolytidae from a surface subject to attack by said scolytids, comprising applying a repellent compound selected from the group consisting of p-anisaldehyde, ethylbenzene, cumene, 4-methoxyacetophenone and mixtures thereof in amounts sufficient to repel said scolytids from said surface or eluting said compound in amounts sufficient to repel said scolytids from said surface from solid supports proximate to said surface from which said scolytids are to be repelled.

2. A method of protecting tree hosts from attack by scolytids comprising applying a repellent compound selected from the group consisting of p-anisaldehyde, ethylbenzene, cumene, 4-methoxyacetophenone and mixtures thereof to trees subject to attack by scolytids in concentrations sufficient to repel said scolytids.

3. The method of claim 2, wherein said tree hosts comprises conifers.

\* \* \* \* \*